US010627803B2

(12) United States Patent
Assmann et al.

(10) Patent No.: US 10,627,803 B2
(45) Date of Patent: Apr. 21, 2020

(54) METHOD AND APPARATUS FOR PRODUCING A MODEL FINDINGS OBJECT

(71) Applicant: Siemens Aktiengesellschaft, München (DE)

(72) Inventors: Stefan Assmann, Erlangen (DE); Susanne Bay, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 414 days.

(21) Appl. No.: 15/051,919

(22) Filed: Feb. 24, 2016

(65) Prior Publication Data
US 2016/0267246 A1 Sep. 15, 2016

(30) Foreign Application Priority Data
Mar. 10, 2015 (DE) .................. 10 2015 204 237

(51) Int. Cl.
G06F 19/00 (2018.01)
G05B 19/4099 (2006.01)
G16H 50/50 (2018.01)
B33Y 50/02 (2015.01)
B29C 64/386 (2017.01)

(52) U.S. Cl.
CPC ......... *G05B 19/4099* (2013.01); *G06F 19/00* (2013.01); *G16H 50/50* (2018.01); *B29C 64/386* (2017.08); *B33Y 50/02* (2014.12); *G05B 2219/35134* (2013.01); *G05B 2219/49007* (2013.01); *Y02P 90/265* (2015.11)

(58) Field of Classification Search
CPC ............... G06F 19/3437; G16H 50/50; G05B 19/4099; G05B 2219/49007; G05B 2219/35134; B29C 64/386; Y02P 90/265; B33Y 50/02

USPC .......................................... 700/98
See application file for complete search history.

(56) References Cited

U.S. PATENT DOCUMENTS

2011/0054354 A1* 3/2011 Hunter ............... A01G 7/00
600/587
2014/0312535 A1* 10/2014 Dikovsky .......... A61C 13/0019
264/401
2015/0105891 A1 4/2015 Golway

FOREIGN PATENT DOCUMENTS

| CN | 201629084 U | * 11/2010 | ............. G09B 23/28 |
| CN | 103932682 | 7/2014 | |
| CN | 104136199 | 11/2014 | |

OTHER PUBLICATIONS www.kunststoffe.de/produkte/uebersicht/beitrag/haptec-haptik-wird-messbar-577718.html.
www.innowep.com.

(Continued)

*Primary Examiner* — Tha-O H Bui
(74) *Attorney, Agent, or Firm* — Harness, Dickey & Pierce, P.L.C.

(57) ABSTRACT

A possibility is to be created of achieving the diagnosis of objects which are difficult to access. To this end, an apparatus and a method are proposed for producing a model findings object, in which image data or images of an original findings object are provided. Geometry data and one or a number of values for at least one material property are obtained from this image data. The model findings object is finally printed via a 3D printing method according to the geometry data with a material according to the value or values of the at least one material property. A physician can then diagnose the model findings object in addition to the images using palpation.

26 Claims, 3 Drawing Sheets

(56) References Cited

OTHER PUBLICATIONS

German Office Action dated Nov. 10, 2015.
Office Action dated May 8, 2018 in Chinese Patent Application No. 2016101335247.
Office Action dated Dec. 12, 2018 in Chinese Patent Application No. 2016101335247.
Third Office Action dated May 24, 2019 in Chinese Patent Application No. 2016101335247.
Office Action dated Dec. 30. 2019 in Chinese Patent Application No. 2016101335247.

* cited by examiner

METHOD AND APPARATUS FOR PRODUCING A MODEL FINDINGS OBJECT

PRIORITY STATEMENT

The present application hereby claims priority under 35 U.S.C. § 119 to German patent application number DE 102015204237.5 filed Mar. 10, 2015, the entire contents of which are hereby incorporated herein by reference.

FIELD

At least one embodiment of the present invention generally relates to a method and/or an apparatus for producing a model findings object. Such a model findings object can be used to create a diagnosis.

BACKGROUND

As a result of their training, physicians are familiar with examining and diagnosing patients using all their senses, inter alia by sensing (palpation). With the diagnosis of radiological images (ultrasound, x-ray, CT, MR, SPECT, PET, etc.) tactile palpatory contact with the patient is in most cases lacking as a further source of information for the findings.

In medicine, examining the body by way of feeling with the fingers or hands is referred to as palpation. Palpation is one of the oldest methods of diagnosis and forms part of a physical examination, just like inspection, auscultation and percussion. Assessed here are the consistency, elasticity, mobility, sensitivity to pain and the size of the organs or body structure to be examined.

Palpation, as it is known, can take place using one or a number of fingers and the palm of the hand. With anatomical structures, which do not lie directly below the skin, clinical diagnostics using palpation is difficult or impossible. Similarly, palpation is hampered in the case of very overweight patients.

Until now, the palpatory findings were not included in the findings of radiological image findings.

The clinical diagnostics of anatomic structures, which are not accessible for palpation, takes place on the basis of translations of CT or MR data into visual information. Radiologists must learn to interpret visual information during years of training.

SUMMARY

At least one embodiment of the present invention includes a method which creates a possibility of improving the diagnosis of image data.

At least one embodiment of the present invention is directed to a method for producing a model findings object, by providing image data of an original findings object, obtaining geometry data and one or a number of values for at least one material property from the image data and printing the model findings object via a 3D printing method according to the geometry data with a material according to the value or the values of the at least one material property.

Moreover, provision is made, according to at least one embodiment of the invention, for an apparatus for producing a model findings object comprising a data storage facility for providing image data of an original findings object, a computing facility for obtaining geometry data and one or a number of values for at least one material property from the image data and a 3D printing device for printing the model findings object according to the geometry data with a material according to the value or values of the at least one material property.

BRIEF DESCRIPTION OF THE DRAWINGS

The present invention is now explained in more detail on the basis of the appended drawings, in which.

Figure 1:
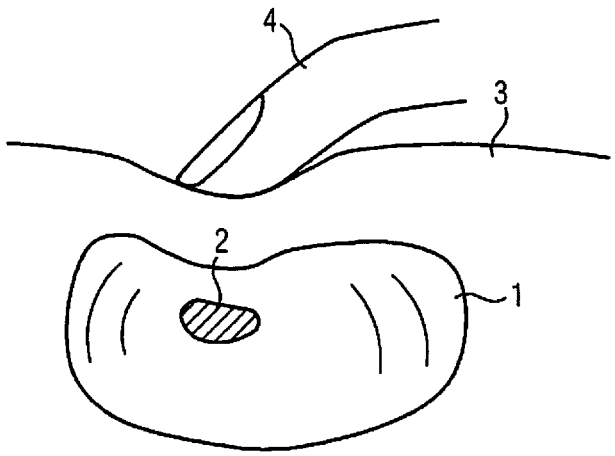
FIG. 1 shows a diagram of the palpation of an internal organ.

The example embodiments illustrated in more detail below represent preferred embodiments of the present invention. It should be noted here that the cited features cannot only be realized in the illustrated combinations, but also alone or in other technically meaningful combinations.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Further, although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

At least one embodiment of the present invention is directed to a method for producing a model findings object, by providing image data of an original findings object, obtaining geometry data and one or a number of values for at least one material property from the image data and printing the model findings object via a 3D printing method according to the geometry data with a material according to the value or the values of the at least one material property.

Moreover, provision is made, according to at least one embodiment of the invention, for an apparatus for producing a model findings object comprising a data storage facility for providing image data of an original findings object, a computing facility for obtaining geometry data and one or a number of values for at least one material property from the image data and a 3D printing device for printing the model findings object according to the geometry data with a material according to the value or values of the at least one material property.

Figure 4:
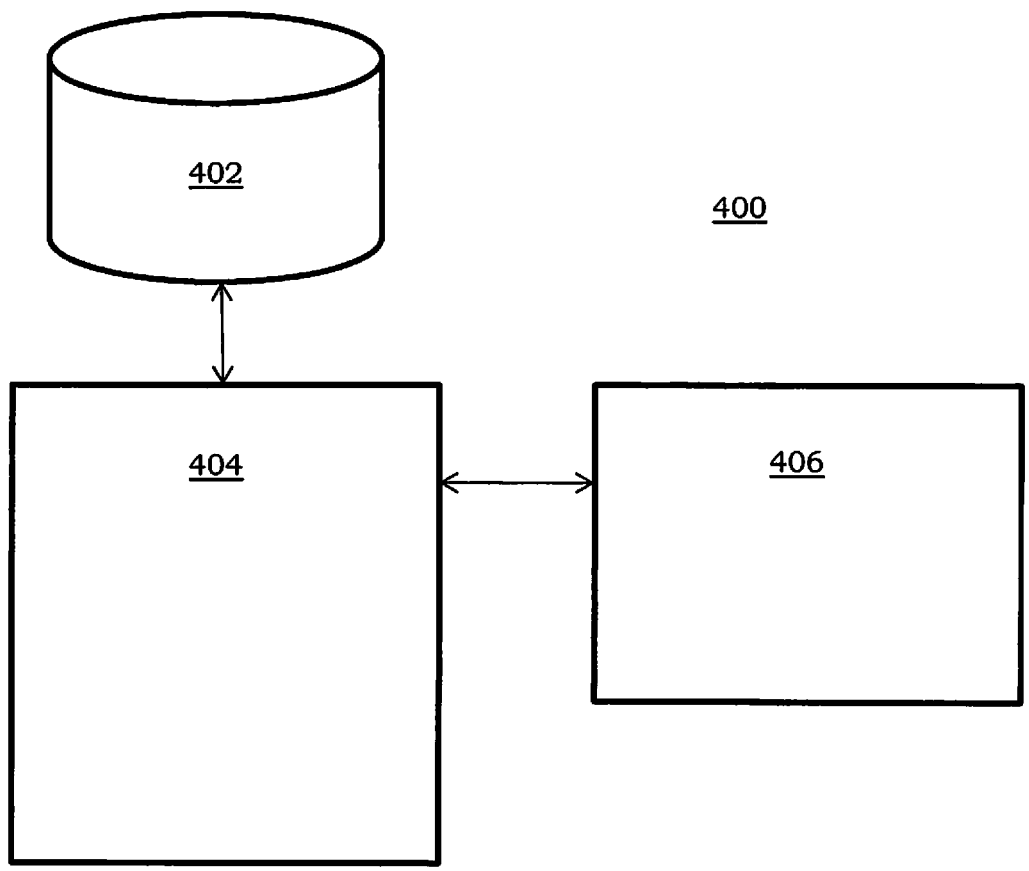
FIG. 4 shows a diagram of an apparatus for producing a model findings object.

Referring to FIG. 4, for an apparatus 400 for producing a model findings object comprising a data storage facility 402 for providing image data of an original findings object, a computing facility 404 for obtaining geometry data and one or a number of values for at least one material property from the image data and a 3D printing device 406 for printing the model findings object according to the geometry data with a material according to the value or values of the at least one material property.

2D or 3D image data which was previously obtained correspondingly is therefore advantageously provided by an original findings object, which may be part of a human body. The geometry data of the original findings object is then reconstructed from the image data. Moreover, a value for at least one material property of the original findings object is also obtained from the image data, or a number of values in this regard is obtained. A 3D print of a model (model findings object) of the original findings object subsequently now takes place. This printed model findings object has a geometry reproduced from the original findings object, at least in parts, and moreover another material property which corresponds to or matches that of the original findings object. This reproduced geometry and material property of the model findings object can help the reporting physician to extend the image findings using palpatory diagnosis.

A number of values for the at least one material property is preferably obtained in a location-dependent manner and the printing takes place with a number of different materials in correspondence with the location-dependent material property. The model findings object thus receives the same or at least one similar location-dependent material property as the original findings object. The reporting physician thus accordingly gains different tactile impressions when sensing different points of the model findings object using his fingers. The location-dependency here not only signifies a two-dimensional location dependency, but instead in particular a three-dimensional location dependency. The model findings object is therefore printed spatially distributed with different materials. The image data can originate at least partly from radiological recordings, in particular from MR recordings or ultrasound recordings. Moreover, x-ray recordings, CT recordings and suchlike can naturally also be used. Image data of this type also in many cases establishes the possibility of a high spatial resolution.

Moreover, the image data can originate at least partly from elastography recordings. Reliable and high-quality elasticity parameters of the original findings object can be obtained from such elastography recordings on the basis of MR or ultrasound.

The at least one material property, for which values are obtained from the image data, can relate to the density or rigidity of an object. For instance, the object can be the entire original findings object or a part thereof. Using palpation, the density becomes indirectly noticeable for instance by way of the weight of the model findings object. Moreover the density or rigidity of an object can provide statements relating to its consistency.

The at least one material property can relate to an elasticity parameter, in particular a modulus of elasticity, a modulus of compression or a yield modulus. The property reflected by the modulus of elasticity is the degree to which a deformation formed by touch returns to normal. The modulus of compression can identify how significantly an object, here the model findings object or a part thereof, can be compressed. The yield modulus finally provides the reporting physician with information relating to the linear elastic deformation of the model findings object or a part thereof.

The geometry data, which is obtained from the image data for the production of the model findings object, can relate to a surface structure and/or an inner structure of the original findings object. A surface roughness of the model findings object can thus be diagnosed using palpation for instance. The geometry data can however also be pure coordinates for controlling the 3D printer.

The value or values for the at least one material property can be obtained via a database or a table on the basis of the image data. This means that the values for the material property can be obtained empirically and in particular by way of so-called look-up tables, which enable a unique assignment of image recording values to values of material properties.

The original findings object can be a human organ or part thereof. In particular, the original findings object can be a liver, a kidney or such like.

The features illustrated above in conjunction with the inventive method can also be transferred to the inventive apparatus as functional features.

FIG. 1 shows the principle of the palpation of a human body. An internal organ such as the liver 1 is to be palpated for instance. Here the liver 1 has a tumor 2, which has different elasticity parameters or properties to the surrounding liver tissue. If necessary, it is possible for a physician to feel this change in the elasticity properties or condition of the liver 1 from the outside. To this end, the physician feels the abdominal wall 3 with his finger 4 for instance. In doing so the physician uses his finger 4 to press into the abdominal wall 3, and if applicable feels the tissue change in the internal organ disposed therebelow. However if the abdominal wall 3 is very thick in the case of an overweight person for instance, tissue changes to internal organs can possibly no longer be sensed. Moreover, organs disposed even further inside, such as the spleen or moving organs such as the heart are however barely or not accessible for palpatory diagnosis.

A further problem area resides in the tactile diagnosis, if only the surface is to be sensed for instance. For instance, changes to bone surfaces (for instance due to inflammations or malformations) can be sensed by running the hand or fingers over bones which are disposed adjacent to the skin surface. Again this may result in problems with more overweight people.

Both palpatory and also tactile diagnoses can be assisted or improved using the present invention. To this end, a model findings object, namely of the object to be diagnosed (also referred to here as original findings object) can be artificially produced, which can then be diagnosed haptically, i.e. in a palpatory and/or tactile fashion.

Figure 2:
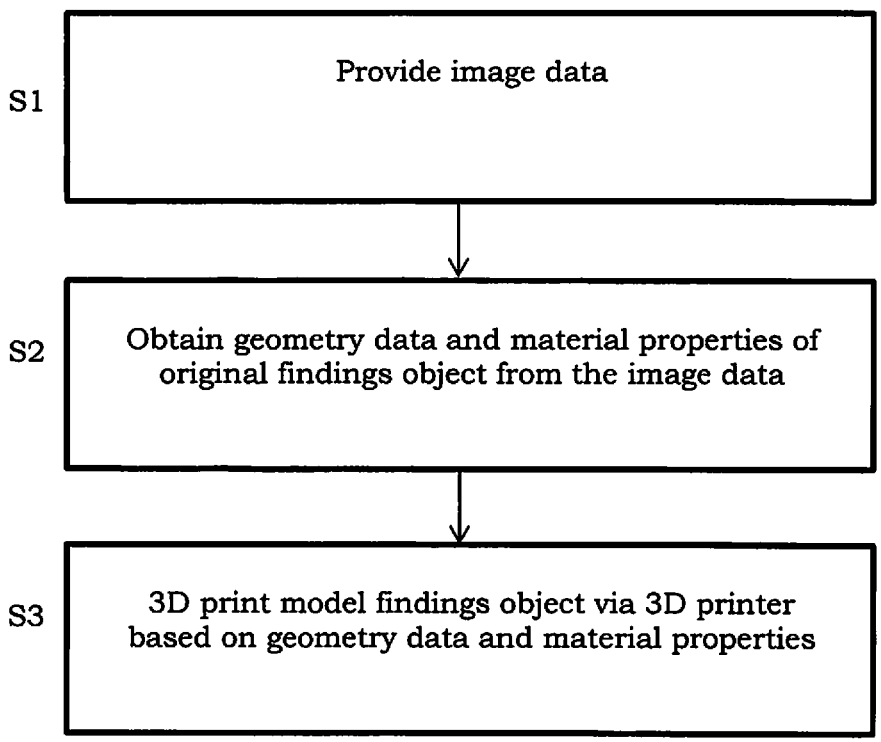
FIG. 2 shows a schematic process flow to produce a model findings object.

To produce a model findings object (e.g. modeled liver) one or a number of images can be obtained in a two or three-dimensional manner via an imaging method. These are preferably radiological images or also other images which make corresponding image data available. The image data is then provided according to FIG. 2 in step S1. This provision either takes place directly via the image recording facility or however by a storage facility in an image processing facility. In a subsequent step S2, geometry data relating to the original findings object is obtained from the image data, in order to be able to produce a 3D model findings object therefrom. This geometry data can be data relating to the external structure or the internal structure of the original findings object. On a logically lower level, the geometry data is simply the 3D coordinates of a smallest volume unit of a 3D image ("voxel") or a 3D model. Moreover, at least one material property of the original findings object is also obtained or determined in step S2 from the image data. Overall, the contour of the original findings object (e.g. liver or a part thereof) and at least one material property for this liver is produced from the image data, or a separate value for the at least one material property is obtained for each voxel from the image data.

In a subsequent step S3, a 3D print based on the geometry data and the value or values takes place for one or a number of material properties. The result of this 3D print is a model findings object, which can be diagnosed by the physician using palpation.

Anatomical target areas (e.g. a liver) can be printed from radiological images via a 3D printer. The printouts also serve as a tactile/palpatory source of information to the reporting physician of the images. They enable a clinician to perform the palpatory diagnosis, which, contrary to interpreting images, he has learnt in his clinical training.

According to one embodiment, the model findings object within the scope of the present image data can be defined in terms of its dimensions or boundaries. To this end, the physician can manually select or segment organs on the radiological images (or in general target structures) using a drawing tool. Only the selected cutout of the images is then modeled or printed. The selection therefore also results in geometry data for the 3D print.

In a further preferred embodiment, the physician can select which tactile-palpatorily important properties from the recorded images are to flow into the 3D print. He can therefore select elasticity parameters from existing elastography recordings of MR or ultrasound as material property, so that these are taken into account accordingly when printing the model findings object. The modulus of elasticity, the modulus of compression and/or the yield modulus serve as elasticity parameters for instance. With the elastography, the object to be examined is cyclically applied with primary waves, which compress and relieve the object alternately. Ultrasound or MR recordings are made synchronous here. If the elastography data, which can display the image data, is now used as the basis of the 3D print, the physician thus receives for instance, in the case of a liver, an image of the liver from materials with the corresponding elasticity and consistency for a tactile/palpatory diagnosis in addition to the pure data from the image recordings.

Alternatively, the user, in particular the physician, can select the density or rigidity of the original findings object as a material property, which is to be represented in the model findings object. Corresponding density/rigidity information can be obtained from existing x-ray images (x-ray absorption (HU values)) or from MR images (e.g. UTE recording (Ultrashort TE), T1/T2/T2*maps or proton density recordings). As a result, the consistency of target areas printed and based on this information can be examined in a tactile/palpatory manner. For instance, the feel of water and which MR signal water delivers is known.

The user can however also select for instance that relief information is to flow into the 3D printer. Relief data from the surface condition or the internal condition of structures (e.g. bones) can thus be obtained from the image data and used for the 3D print. The corresponding surface condition can then be sensed in a tactile manner on the model findings object by the physician.

To produce the model findings object, the apparatus is optionally equipped with an input device, with which the physician can specify or indicate which structures within the 3D print he would like to touch with his fingers (e.g. which sectional planes of the original findings object). The 3D print will thereupon take place such that the printout can be destroyed in order to enable the sensing of the predefined internal structures and also reproduce them again.

According to a further possibility, the physician can select from a database, which properties a typical organ or typical target structure has, in order to enable a comparison with a standard diagnosis. He therefore receives for instance from the database, information relating to the elasticity or brittleness of bones or organs of patients of a similar age or state or clinical picture. If necessary, even model findings objects of healthy people are available to the physician within the scope of such a "database".

Modern plastics can be used to perceive and model various material qualities or material properties such as viscoelasticity. For each layer or sublayer, which is applied in the 3D print, the respectively suitable plastic can be selected. Catalogs are available, which reproduce the individually processable plastics and their material properties.

The fact that plastics have various properties relating to surface feel also indicates the research in the field of PDAs, mobile telephones or vehicle steering wheels. The tactile surface appearance plays an essential role for the quality rating. As material properties of significant importance, the micro- and macrostructure of the surfaces and also functional properties such as microfriction, deformability and elasticity behavior play an important role. In this regard, variables relating to tactile sensation could be determined electronically, by the physical properties of significance to the surface feel having been transferred into numerical key characteristics (cf. for instance the company Innoweb Mess and Prueftechnik [Measurement and test engineering]).

Figure 3:
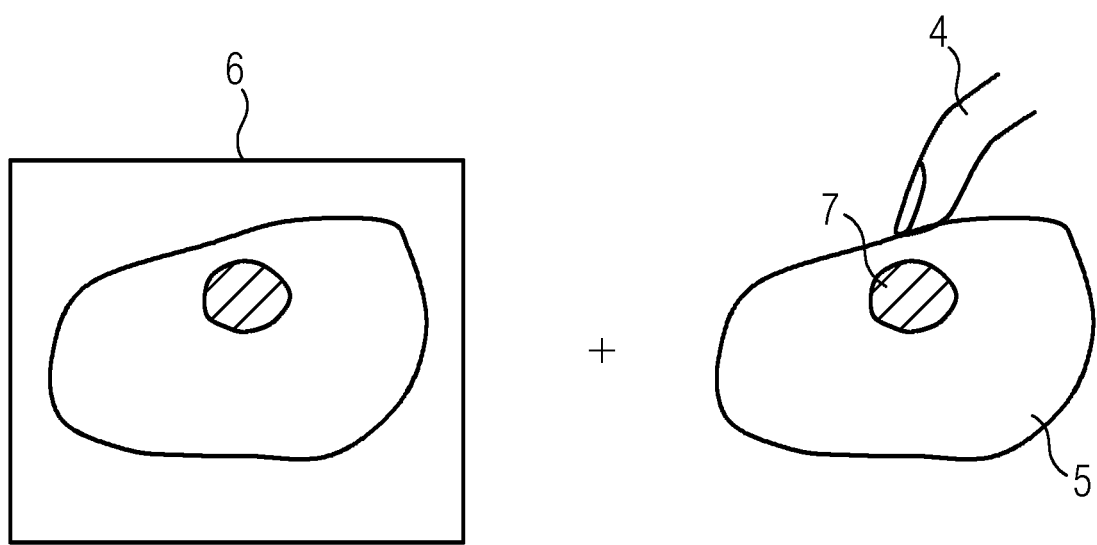
FIG. 3 shows a diagram relating to the diagnosis with the aid of an image and a model findings object.

As shown in FIG. 3, the physician receives an additional source of information for the palpation relating to the diagnosis of the radiology images 6, which are obtained in a conventional manner, by the printout 5 (model findings object) of anatomical structures with properties which mirror the actual conditions (original findings object 1). In the example in FIG. 3, the image 6 shows a radiological recording of the liver 1 including the tumor 2 of FIG. 1 for instance. The printed model findings object 5 represents a model of the liver 1, wherein a section 7 corresponding to the tumor 2 is also disposed here at the corresponding point of the model findings object 5. This section 7 has the same modulus of elasticity as that of the actual tumor 2 for instance. The material of the model findings object 5 surrounding the section 7 conversely has the modulus of elasticity of the healthy liver tissue. The example of FIG. 3 can naturally be transferred to other objects or original findings objects and material properties.

Using palpation, the physician can now sense the elasticity or rigidity of the tissue or lesions within the tissue for instance. In order to interpret this source of information (model findings object) a clinician who is not practiced in the interpretation of radiological images, can therefore resort to his experience in the physical examination of the patient and need not learn the ropes of another modality (the interpretation of visual information in the radiological images).

The aforementioned description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for examining a model findings object, the method comprising:
   receiving a selection from an external source, the selection including at least one material property among a plurality of material properties;
   determining geometry data and one or more values of the at least one material property of an original findings object based on image data of the original findings object, the original findings object including a tumor; and
   printing the model findings object via a 3D printer according to the geometry data, using one or more materials according to the one or more values of the at least one material property such that an operator is able to detect the tumor by physically palpating the model findings object.

2. The method of claim 1, wherein
   the one or more values of the at least one material property are location-dependent; and
   the printing prints different materials of the one or more materials in correspondence with the location-dependent one or more values of the at least one material property.

3. The method of claim 2, wherein the image data originates at least partly from radiological recordings.

4. The method of claim 3, wherein the radiological recordings are MR recordings or ultrasound recordings.

5. The method of claim 2, wherein the image data originates at least partly from elastography recordings.

6. The method of claim 1, wherein the image data originates at least partly from radiological recordings.

7. The method of claim 6, wherein the radiological recordings are MR recordings or ultrasound recordings.

8. The method of claim 1, wherein the image data originates at least partly from elastography recordings.

9. The method of claim 1, wherein the at least one material property relates to a density or a rigidity of at least a portion of the original findings object.

10. The method of claim 1, wherein the at least one material property relates to an elasticity parameter.

11. The method of claim 1, wherein the geometry data relates to at least one of a surface structure or an internal structure of the original findings object.

12. The method of claim 1, wherein the one or more values of the at least one material property are determined based on the image data and a database or a table.

13. The method of claim 1, wherein the original findings object is at least a portion of a human organ.

14. The method of claim 1, wherein the plurality of material properties includes a modulus of elasticity, a modulus of compression and a yield modulus.

15. The method of claim 1, further comprising:
   receiving a selected geometry data type from the external source, the selected geometry data type including one or both of surface geometry data or internal geometry data,
   wherein the determining geometry data determines the geometry data of the original findings object based on the image data and the selected geometry data type.

16. The method of claim 15, wherein
the selected geometry data type includes both the surface geometry data and the internal geometry data, and
the determining geometry data determines both the surface geometry data and the internal geometry data of the original findings object.

17. The method of claim 16, wherein the at least one material property includes a modulus of elasticity, a modulus of compression and a yield modulus.

18. The method of claim 1, wherein
the plurality of material properties are a modulus of elasticity, a modulus of compression, a yield modulus, and a density or a rigidity of at least a portion of the original findings object; and
the determining determines one or more values of only the at least one material property among the plurality of material properties according to the selection.

19. An apparatus for producing a model findings object, comprising:
a memory having computer-readable instructions stored thereon;
one or more processors communicatively coupled to the memory and configured to execute the computer-readable instructions to
receive a selection from an external source, the selection including aha plurality of material properties, the plurality of material properties including a modulus of elasticity, a modulus of compression and a yield modulus, and
determine geometry data and one or more values of the plurality of material properties of an original findings object based on image data of the original findings object, the original findings object including a tumor; and
a 3D printing facility configured to print the model findings object according to the geometry data, using one or more materials according to the one or more values of the plurality of material properties such that an operator is able to detect the tumor in the original findings object by physically palpating the model findings object.

20. The apparatus of claim 19, wherein
the one or more values of the plurality material properties are location-dependent; and
the 3D printing facility is further configured to print different materials of the one or more materials in correspondence with the location-dependent one or more values of the plurality of material properties.

21. The apparatus of claim 19, wherein the image data originates at least partly from radiological recordings.

22. The apparatus of claim 19, wherein the image data originates at least partly from elastography recordings.

23. The apparatus of claim 19, wherein the plurality of material properties includes the modulus of elasticity, the modulus of compression, the yield modulus, and a density or a rigidity of at least a portion of the original findings object.

24. The apparatus of claim 19, wherein the geometry data relates to at least one of a surface structure or an internal structure of the original findings object.

25. The apparatus of claim 19, wherein the one or more values of the plurality of material properties are determined based on the image data and a database or a table.

26. The apparatus of claim 19, wherein the original findings object is at least a portion of a human organ.

* * * * *